(12) United States Patent
Falleboe et al.

(10) Patent No.: US 11,083,834 B2
(45) Date of Patent: Aug. 10, 2021

(54) EMERGENCY STOP FOR A SYSTEM AND A METHOD FOR ANAL AND/OR STOMAL IRRIGATION

(71) Applicant: Coloplast A/S, Humlebaek (DK)

(72) Inventors: Hans Falleboe, Gentofte (DK); Marie Svane Rizk Vestergård, Frederiksberg (DK)

(73) Assignee: Coloplast A/S, Humlebaek (DK)

( * ) Notice: Subject to any disclaimer, the term of this patent is extended or adjusted under 35 U.S.C. 154(b) by 402 days.

(21) Appl. No.: 16/062,111

(22) PCT Filed: Dec. 16, 2016

(86) PCT No.: PCT/DK2016/050442
§ 371 (c)(1),
(2) Date: Jun. 14, 2018

(87) PCT Pub. No.: WO2017/101954
PCT Pub. Date: Jun. 22, 2017

(65) Prior Publication Data
US 2018/0369474 A1    Dec. 27, 2018

(30) Foreign Application Priority Data

Dec. 17, 2015 (DK) .......................... PA 2015 70833

(51) Int. Cl.
*A61M 3/02* (2006.01)
(52) U.S. Cl.
CPC ........ *A61M 3/0258* (2013.01); *A61M 3/0208* (2014.02); *A61M 3/0295* (2013.01);
(Continued)

(58) Field of Classification Search
CPC .... A61M 3/02; A61M 3/0208; A61M 3/0262; A61M 3/0258; A61M 3/0237;
(Continued)

(56) References Cited

U.S. PATENT DOCUMENTS

2006/0224349 A1* 10/2006 Butterfield ............... G01K 7/42
702/130
2010/0022822 A1   1/2010 Walshe
(Continued)

FOREIGN PATENT DOCUMENTS

CN         2444603 Y     8/2001
CN       203174732 U     9/2013
(Continued)

*Primary Examiner* — Tiffany Legette
(74) *Attorney, Agent, or Firm* — Coloplast Corp., Coloplast A/S; Nick Baumann

(57) ABSTRACT

A system for anal and/or stomal irrigation comprises a reservoir (102) for an irrigating liquid, a catheter (100) comprising a catheter tip for insertion into the rectum and/or stoma of a user and for expelling of the irrigating liquid from the catheter tip, the catheter further comprising an expandable retention element (104), such as a balloon. A pump (101) is provided to pump the irrigating liquid from the reservoir to the catheter tip, and a user-operable control interface (123;125) comprising a dedicated emergency stop zone (125) is provided for receiving user input to withdraw the irrigating liquid from the retention element (100) for purging thereof in any operational state of the system.

11 Claims, 15 Drawing Sheets

(52) U.S. Cl.
CPC . *A61M 2205/3368* (2013.01); *A61M 2205/36* (2013.01); *A61M 2205/50* (2013.01); *A61M 2205/502* (2013.01); *A61M 2210/1064* (2013.01); *A61M 2210/1067* (2013.01)

(58) Field of Classification Search
CPC ........ A61M 3/0254; A61M 2205/3368; A61M 2205/36; A61M 2205/50; A61M 2205/502; A61M 2210/1064; A61M 2210/1067
See application file for complete search history.

(56) References Cited

U.S. PATENT DOCUMENTS

| | | | |
|---|---|---|---|
| 2010/0185142 A1* | 7/2010 | Kamen | A61M 5/16809 604/66 |
| 2010/0312039 A1* | 12/2010 | Quirico | A61N 5/1075 600/4 |
| 2012/0143168 A1* | 6/2012 | Bjerregaard | A61M 3/0295 604/514 |
| 2013/0245599 A1* | 9/2013 | Williams | A61M 1/006 604/503 |
| 2014/0005602 A1* | 1/2014 | Andreen | A61M 3/02 604/98.02 |
| 2014/0155864 A1* | 6/2014 | Andreen | A61M 3/02 604/514 |

FOREIGN PATENT DOCUMENTS

| | | |
|---|---|---|
| CN | 203815952 U | 9/2014 |
| CN | 204219491 U | 3/2015 |
| CN | 104665850 A | 6/2015 |
| EP | 2671601 A1 | 12/2013 |
| EP | 2679259 A1 | 1/2014 |
| RU | 2532502 C2 | 11/2014 |
| WO | 04006993 A1 | 1/2004 |
| WO | 2006114637 A2 | 11/2006 |
| WO | 11023196 A1 | 3/2011 |
| WO | 2011100170 A1 | 8/2011 |
| WO | 11135557 A1 | 11/2011 |

\* cited by examiner

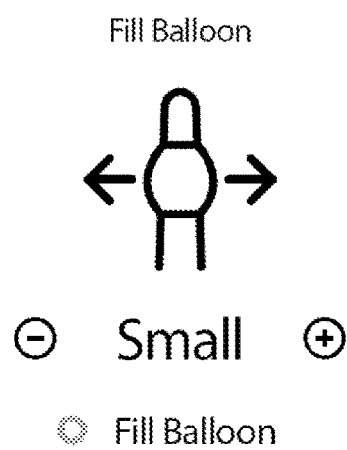

Fig. 9a

Fill Balloon

⊖ Small ⊕

○ Fill Balloon

Settings Saved!

Your default settings has been saved. You can allways access your default setttings by pressing ⊖ & ⊕ simultaneously.

○ Proceed

Fig. 9b

System Settings

| | |
|---|---|
| Language | En |
| Units | ml |
| Catheter | Small |
| Balloon Size | Regular |
| Water Volume | 600ml |

○ Save

Fig. 9c

Starting up

Fig. 10a

Battery OK

The unit is charged press ⏻ to start

Fig. 10b

Preperation

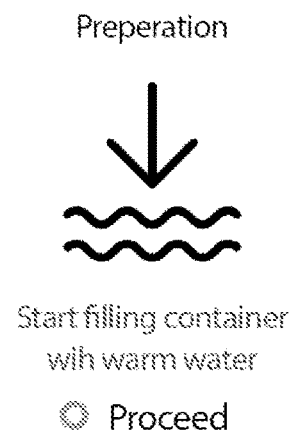

Start filling container wih warm water

○ Proceed

Fig. 10c

Water Temperature
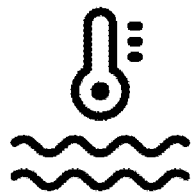
Measuring water
temperature
Fig. 11a
Water Temperature
Too Hot!
Add cold water
to proceed
Fig. 11b
Water Temperature
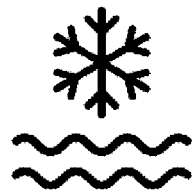
Too Cold!
Add warmer water
 Proceed
Fig. 11c
Water Temperature
Perfect!
 Proceed
Fig. 11d
Preperation
Connect the catheter
to the end of the tube
 Proceed
Fig. 12a
Preperation
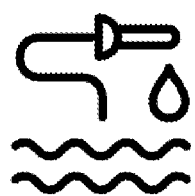
Start water pump to
fill tubes & catheter
 Fill Tubes
Fig. 12b Filling Paused ⊖ Small ⊕

○ Resume

Infusing Water...

⊖ 400ml ⊕
/ 500ml

○ Pause

Infusion Paused

⊖ 400ml ⊕
/ 500ml

○ Resume

Infusion Done

⊖ 0ml ⊕
/ 500ml

○ Proceed

Empty Balloon

Hold on to catheter
while emptying

○ Empty

● Empty Balloon

Hold on to catheter
while emptying

‹ Back    ○ Empty

Emptying Balloon...
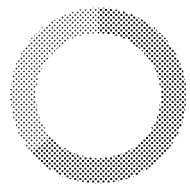
Balloon
○ Pause
Fig. 14l
Emptying Paused
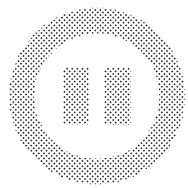
Balloon
○ Resume
Fig. 14m
Remove Catheter
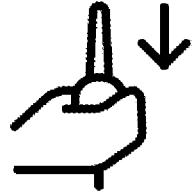
Remove and dispose of catheter
○ Proceed
Fig. 14n
Clean Up
Place end of the tube in sink before draining
○ Drain
Fig. 14o
Draining Tubes...
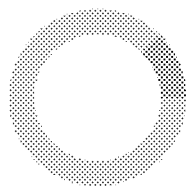
Press Done when tubes are empty
○ Done
Fig. 14p
Save Changes?
Balloon Size    Small
Water Volume    700ml
⊖ No    Yes ⊕
Fig. 14q End Session
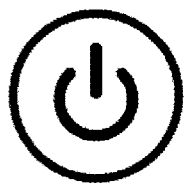
Press ⏻ to power off
Have a nice day!
Fig. 14r
Notification
System has almost reached its maximum usage, please contact your doctor/nurse for a replacement unit,
or
Call support team
0045 123 456 78
Fig. 15a
Error Message
System Failure
0441
Call support team
0045 123 456 78
Fig. 15b

EMERGENCY STOP FOR A SYSTEM AND A METHOD FOR ANAL AND/OR STOMAL IRRIGATION

TECHNICAL FIELD

Provided are a system and a method for anal and/or stomal irrigation comprising a reservoir for an irrigating liquid, a catheter comprising a catheter tip for insertion into the rectum and/or stoma of a user, and an expandable retention element, such as an expandable balloon, for fixation of the catheter tip within the user's rectum or stoma. Further provided are a valve and tubing system for controlling the supply of the irrigating liquid to the catheter tip as well as the supply and the withdrawal of the irrigating liquid to and from the expandable retention element. In particular, a user controlled relief valve is provided.

DETAILED DESCRIPTION

Control of voluntary bowel functions is frequently limited or absent in patients suffering from certain disabilities, such as spinal injuries, multiple sclerosis or bifid spine. Such lack of control of voluntary bowel functions typically results in faecal incontinence or intractable constipation, as patients have significantly reduced ability to sense the presence of faeces in the colon terminal part and the rectum and to sense the evacuation stimulus. Patients having undergone stomal surgery wherein a catheterizable stoma is constructed may suffer from similar difficulties.

It is known to accomplish bowel emptying by irrigation (i.e. flushing) of the rectum or stoma, by an irrigating fluid, such as tap water or saline, which is provided through an intermittent catheter with a tip which is configured and sized for insertion into the rectum or stoma, where it remains in a fixed position by an expandable inflation element, such as a balloon. The balloon may be inflatable by air or by water. Once the rectum or stoma has been flushed with the irrigating liquid, the expandable retention element is allowed to collapse to its non-deflated state, allowing the catheter to be withdrawn from the rectum or stoma, and allowing the liquid and faeces to evacuate. The catheter is connected to a reservoir of the irrigating liquid through a tube, and a pump may be provided for displacing the irrigating liquid from the reservoir to the catheter.

It is an object of embodiments to improve known systems further, in particular by improving a sense of security and user-convenience in relation to self-irrigation, and more particularly by improving user controllability of the system.

Embodiments provide a system for anal and/or stomal irrigation comprising:
  a reservoir for an irrigating liquid;
  a catheter comprising a catheter tip for insertion into the rectum and/or stoma of a user and for expelling of the irrigating liquid from the catheter tip, the catheter further comprising an expandable retention element for fixation of the catheter tip within the user's rectum or stoma;
  a tubing system providing a first conduit for the irrigating liquid between the reservoir and the catheter and providing a second conduit for the irrigating liquid between the reservoir and the expandable retention element;
  a valve system in the second conduit for controlling the flow of the irrigating liquid between the reservoir and the expandable retention element;
  a pump operable to pump the irrigating liquid from the reservoir to the catheter tip;
and
  the pump and the valve system being controllable to selectively:
    pump the irrigating liquid into the expandable retention element for expansion thereof;
    pump the irrigating liquid through the catheter for expelling of the irrigating fluid from the catheter tip and into the user's rectum or stoma;
    withdraw the irrigating liquid from the retention element for purging thereof;
  a user-operable control interface comprising a dedicated emergency stop zone for receiving user input, wherein in response to said user input, the pump and valve system is operable to withdraw the irrigating liquid from the retention element for purging thereof;
wherein said dedicated zone is accessible in any operational state of the system.

Furthermore, embodiments provide a method of operating a system for anal and/or stomal irrigation, said system comprising:
  a reservoir for an irrigating liquid;
  a catheter comprising a catheter tip for insertion into the rectum and/or stoma of a user and for expelling of the irrigating liquid from the catheter tip, the catheter further comprising an expandable retention element for fixation of the catheter tip within the user's rectum or stoma;
  a tubing system providing a first conduit for the irrigating liquid between the reservoir and the catheter and providing a second conduit for the irrigating liquid between the reservoir and the expandable retention element;
  a valve system in the second conduit for controlling the flow of the irrigating liquid between the reservoir and the expandable retention element;
  a pump operable to pump the irrigating liquid from the reservoir to the catheter tip;
said method comprising controlling and operating the pump and the valve system to selectively:
  pump the irrigating liquid into the expandable retention element for expansion thereof;
  pump the irrigating liquid through the catheter for expelling of the irrigating fluid from the catheter tip and into the user's rectum or stoma;
  withdraw the irrigating liquid from the retention element for purging thereof;
a user-operable control interface comprising a dedicated emergency stop zone for receiving user input, wherein in response to said user input, the pump and valve system is operable to withdraw the irrigating liquid from the retention element for purging thereof;
wherein said dedicated zone is accessible in any operational state of the system.

The pump may be manually or electrically driven. The ability of the pump and the valve system to withdraw the irrigating liquid from the retention element for purging thereof allows the retention element to be purged in a controlled manner. Expansion of the retention element as well as collapsing thereof may hence be accurately controlled by adequate control of the pump and the valve system. Collapsing of the retention element by a controlled action, notably by forced purging caused by a pumping action of the pump enables purging of the retention element even under circumstances, at which the retention element is expanded by a relatively low pressure, which is too low for the irrigating liquid to escape from the retention element merely be opening a valve of the valve system. This is particularly advantageous in the case when the user has reduced dexterity and strength in the fingers and arms as it may not be possible for such users to withdraw the catheter even at relatively low pressure in the retention element.

The pump is preferably an electrically driven pump, and the pump and the valve system are preferably controllable by an electronic control system.

The valve system and the tubing system may be configurable to withdraw the irrigating liquid from the retention element during purging thereof by conveying the irrigating liquid from the retention element directly into user's rectum or stoma without the irrigating liquid passing into or through the reservoir. This incurs several benefits. Firstly, the user is released from encountering the possibly disturbing or uncomfortable experience of noting that irrigating liquid passes from the retention element, which is fixed in the user's rectum or stoma, back to the reservoir. Accordingly, user comfort and trust in the system is improved. Secondly, as a temperature equilibrium will be achieved between the irrigating liquid within the expanded retention element and the user's body while the retention element is fixed within the bowel, the irrigating liquid used for expansion may conveniently be used for irrigation (i.e. flushing of the bowel) without the need for any further temperature management for that part of the irrigating liquid. Thirdly, the distance to be travelled by the irrigating liquid and hence power consumption of the pump may be minimized when the irrigating liquid is allowed to pass directly from the retention element to the catheter tip for irrigation of the bowel.

Alternatively, however, the pump, the valve system and the tubing system may be configurable to withdraw the irrigating liquid from the retention element during purging thereof by conveying the irrigating liquid from the retention element into the reservoir.

Recent studies have shown that users of anal and/or stomal irrigation systems comprising pumps may sometimes experience pain and discomfort associated with irrigation. This may be caused by an improper positioning of the catheter tip, a condition in the stoma etc. When the user experience pain, it is important to be able to abort irrigation and collapse the retention element to withdraw the catheter from the rectum or stoma of the user. The dedicated emergency stop zone for receiving user input to control withdrawal of irrigation liquid from the retention element allows the user to collapse the retention element in any operational state of the system. Thus, it may advantageously be achieved that removal of the retention element and catheter from the rectum or stoma may be effected swiftly and conveniently. This improves the sense of security and convenience for users of anal and/or stomal irrigation systems.

The pump may comprise a reversible electrical pump, which is operable in one direction to pump the irrigating liquid into the expandable retention element for inflation thereof, and which is operable in a reverse direction to withdraw the irrigating liquid from the expandable retention element for collapsing thereof in response to the user input in the user-operable control interface. In this case, the pump is configured to both pump irrigating liquid into the retention element and to actively withdraw irrigating liquid from the retention element. Moreover, the pump can be reversed to apply suction to the retention element. In this way it is ensured that the retention element may be collapsed caused by a pumping action even under circumstances, at which the retention element is expanded by a relatively low pressure, which is too low for the irrigating liquid to escape from the retention element merely be opening a valve of the valve system.

Furthermore, reversing an electrical pump may be achieved by simply changing the direction of the current powering the pump using an electronic control system. Such switching of current direction may be done independently of the configuration of the valve system. Thus the time it takes to collapse the retention element and allow the catheter to be removed from the rectum or stoma of the user may be further minimized. Also, as between providing pressure or suction to irrigating liquid in the retention element without changing the configuration of the valve system reliefs the valve system from mechanical stress in relation to valve configuration change. Additionally, providing the reversible electrical pump is a cost effective and simple way of providing means of actively withdrawing irrigating liquid from the retention element. Thus, the cost of this added ability of the system may be minimized.

In order to enhance convenience and enable fast operation, the control interface may be configured to recognize a single user action as being said user input. In this case the irrigating system allows the user to withdraw liquid from the retention element by a single action. A single user action may be depressing a button, touching a touch-sensitive user-interface, flipping a switch etc. This is advantageous as the time it takes to remove the catheter is further minimized. Also, the dexterity and strength of catheter users may be reduced, in which case it is particularly important to provide easily accessible means of withdrawing liquid from the retention element.

The dedicated emergency stop zone may comprise a user-operable button. Also, the control interface may be configured to recognize a depression of the user-operable button as being the user input.

In this case, the user-operable button may be clearly marked and labelled for quick identification. The user may then quickly locate and depress the user-operable button for withdrawing irrigating liquid from the retention element to enable removal of the catheter from the user's rectum or stoma. The presence of the user-operable button may add to the comfort of the user even in cases when it is not necessary to actively withdraw irrigating liquid from the retention element. That is, the user may be reminded that it is possible to quickly enable removal of the catheter from the rectum or stoma of the user if necessary. Such reminder may add to the comfort of use and add to the user's trust in the system.

The user-operable button may comprise a mechanical button. Depressing a mechanical button provides tactile feedback to the user, which may give the user a sense of recognition and comfort. Also, the mechanical button may be depressed irrespective of whether or not the user e.g. wears gloves or has wet fingers. Thus, providing a mechanical button for controlling withdrawal of irrigating liquid from the retention element may add to the comfort and convenience of the user.

The user-operable control interface may comprise a graphical user-interface. Also, the system may comprise a control system comprising a memory for storing information to be presented by the graphical user-interface. The graphical user-interface may be configured to display a variety of information. The graphical user-interface may further be configured with a touch-sensitive area for receiving user input. The graphical user-interface may present data on parameters relevant to the user and receive versatile user input to control the system. This may allow the user to control the system in a convenient and time efficient manner even if the system is providing with a number of settings and modes available to the user.

A thermo sensor may further be provided, which is connected to the reservoir for obtaining a measure of a temperature within the reservoir, the tubing system and/or the catheter. The control system may be operatively connected with the thermo sensor, and the control system may be configured to determine a temperature within the reservoir before the irrigating liquid is filled or re-filled into the reservoir, determine an initial change of the temperature within the reservoir upon commencement of filling or refilling of the irrigating liquid into the reservoir, and predict a future asymptotic value of the temperature within the reservoir on the basis of at least the initial change. The control system may further be configured to continuously determine a current temperature or a current rate of change of the temperature within the reservoir while the irrigating liquid is filled or refilled into the reservoir, and to continuously update the prediction of the future asymptotic value of the temperature within the reservoir on the basis of at least said current temperature and/or rate of change of the temperature.

Thanks to the thermo sensor and the control system, a prediction of the future asymptotic value of the temperature within the reservoir once filled, notably of the irrigating liquid, may be made. As the prediction of the future asymptotic temperature value is continuously updated on the basis of the current temperature and/or the rate of change of temperature, a change of temperature of the liquid supplied to the reservoir, such as for example a change of the ratio between hot and cold tap water, is adequately reflected in the temperature prediction.

The graphical user-interface may be configured to notify a user if a current or predicted temperature of the irrigating fluid is not within a predetermined temperature interval, thus allowing the user to ascertain if the temperature of the supplied liquid, typically tap water, is to be increased or decreased.

The user-operable control interface may comprise system user operation instructions and the graphical user-interface may be configured to show said user operation instructions, which will allow the user to conveniently retrieve user operation instructions without the need to consult a separate manual.

The graphical user-interface may be configured to show a system operational state status. Such information may include the current state of operation as well as the status of the current state of operation. In this case, the user is able to readily assert operation of the system and correlate body sensations with the current mode of operation. This may provide the user with increased comfort in relation to irrigation and trust in the system. Furthermore, the status of the current mode of operation may also inform the user when current mode of operation is expected to finish, adding to the convenience of using the system.

The graphical user-interface is configured to notify the user that a cleaning sequence is scheduled in predetermined intervals. For optimal operation and function of the system it is advantageous to perform cleaning sequences in predetermined intervals. The intervals may also be determined in response to operational status of individual components. By allowing the graphical user-interface to notify such cleaning sequences, it may be ensured that the system is cleaned accordingly. The cleaning sequence may be manually performed by the user according to instructions displayed on the graphical user-interface or the system may be configured to perform the cleaning sequence automatically.

The graphical user-interface may be configured to notify the user that the system is scheduled to be replaced after a predetermined number operational cycles, which may further help to prevent inconvenience related to system malfunctions due to excessive use.

The valve system within the tubing system is preferably configured to selectively cause one flow configuration selected from a first, second and third flow configuration at a time, wherein:
  the first flow configuration is arranged to cause a transfer the irrigating liquid, by means of said pump, from the reservoir into the expandable retention element;
  the second flow configuration is arranged to transfer the irrigating liquid, by means of said pump, from the reservoir to the catheter;
  the third flow configuration is arranged to transfer the irrigating liquid, by means of said pump, away from the expandable retention element.

Thus, in the first flow configuration the irrigating liquid is transferred from the reservoir to the expandable retention element for expansion thereof. In the second flow configuration, the irrigating liquid is transferred from the reservoir to the catheter, i.e. to the catheter tip for insertion into the user's rectum or stoma. In the third flow configuration, the irrigating liquid is transferred away from the expandable retention element, either directly to the catheter tip for flushing of the user's bowel without the irrigating liquid passing into or through the reservoir, or back to the reservoir.

As further means to control the pressure in the expandable retention element in a convenient manner, a first relief valve may be provided, the valve being configured to open if pressure in a bowel of the user exceeds a first threshold limit in the first flow configuration, i.e. during expansion of the expandable retention element. Preferably, when the first relief valve opens, an amount of the irrigating liquid is transferred to the reservoir or expelled into a toilet facility if the valve, for instance, is placed in a connector portion of the catheter.

A second relief valve may be provided as a further or alternative security measure, the second relief valve being configured to open if pressure in a bowel of the user exceeds a second threshold limit in the second flow configuration, i.e. during flushing of the user's bowel, so as to transfer an amount of the irrigating liquid to the reservoir or expel it into a toilet rather than keeping pumping irrigating liquid into the user's rectum or stoma.

In general, it may be desirable to transfer liquid to be expelled due to overpressure out of the system, i.e. into a toilet facility, rather than into the system itself, such as into the reservoir.

Generally, the valve and tubing system may be operable to redirect the irrigating liquid to the reservoir if the pressure within the expandable retention element exceeds a predetermined threshold level.

In order to further control the supply of the irrigating liquid to the expandable retention element and/or to the catheter, the system may comprise:
  a first actively controllable valve arranged in the tubing and/or the catheter at a position between the pump and the expandable retention element; and/or
  a second actively controllable valve arranged in the tubing at a position between pump and the catheter.

The actively controllable valves are operable in order to achieve the desired one of the first, second and third flow configuration. More specifically, when the first actively controllable valve is open and the second one is closed, irrigating liquid may pass to the expandable retention from the reservoir, or away from the expandable retention element. In the state wherein the first valve is open and the second is closed, the direction of flow through the pump may be controllable by the direction of rotation of the pump motor. The destination of irrigating liquid forced away from the expandable retention element may be selected by one or more passively controllable valves, such as check valves, or by one or more actively controllable valves. When the first actively controllable valve is closed and the second one is open, irrigating liquid may pass from the reservoir to the catheter without entering the expandable retention element.

At least one check valve is preferably provided for preventing a backflow of the irrigating liquid from the pump in a direction towards the reservoir, so as to force liquid withdrawn from the expandable retention element towards the catheter and into the user's rectum or stoma.

A user-operable control interface may be provided for controlling operation of the valve system and/or the pump. The user may for example select valve settings to select a flow configuration among the above-mentioned first, second and third flow configurations, and the user may further set operating parameters of the system, such as expansion pressure of the retention element, or an operating speed of the pump, i.e. flow rate of irrigating liquid for irrigation, or an irrigation duration.

In one embodiment, the pump is operable to repeatedly expand and collapse so as to stimulate the peristaltic of the user's bowel. Such action of the pump may be activatable by the user through the control interface. Its settings, such as duration or frequency of repeated expansion and collapsing may be defined through the interface. The expandable retention element may be incrementally expandable or collapsible, allowing the user to control expansion or collapsing of the retention element in response to the user's sensation of the state of expansion.

The control system may be configured to control a flow condition of the irrigating liquid at the catheter tip during anal or stoma irrigation. The control system may hence comprise a controller for controlling operation of the pump, at least one sensor for determining a measure of pressure at at least one first predetermined position in the tubing system and/or the catheter during operation of the pump, and a processor for determining or estimating said flow condition at the catheter tip on the basis of said measure of pressure. Further, the control system may be configured to control the pumping operation of the pump in response to said measure of pressure.

The provision of the at least one sensor for determining a measure of pressure at at least one first predetermined position in the tubing system and/or the catheter during operation of the pump allows the processor to determine or estimate a flow condition at the catheter tip on the basis of such measure. For example, the rise of the pressure at a particular flow restrictor within the tubing system to a predetermined level may indicate the presence of irrigating liquid at the tip of the catheter. Similarly, the rise of pressure at the catheter tip itself may indicate the presence of irrigating liquid at the tip.

In one embodiment, the control system may comprise a memory for storing at least one pressure threshold value indicative of the presence of the irrigating liquid at at least the first predetermined position in the tubing system and/or the catheter and/or at at least one second predetermined position in the tubing system and/or the catheter. In such an embodiment, the control system may be configured to continue the pumping operation of the pump for a limited period of time after determination, by the at least one sensor, of a pressure value at the at least one first predetermined position which is at least equal to the pressure threshold value or a value derived therefrom. For example, one of the first and second predetermined positions may be a position at the catheter tip or in the vicinity thereof, in which case the control system may be configured to continue said pumping operation for a certain duration after the determination of said pressure threshold value. Accordingly, the amount of irrigating liquid expelled from the catheter tip may be accurately controlled by control of said duration.

BRIEF DESCRIPTION OF THE DRAWINGS

Embodiments will now be further described with reference to the accompanying drawings, in which:

FIGS. 9a-15b illustrates display configurations of a graphical user interface of a user-operable control interface.

DETAILED DESCRIPTION OF THE DRAWINGS

Figure 1:
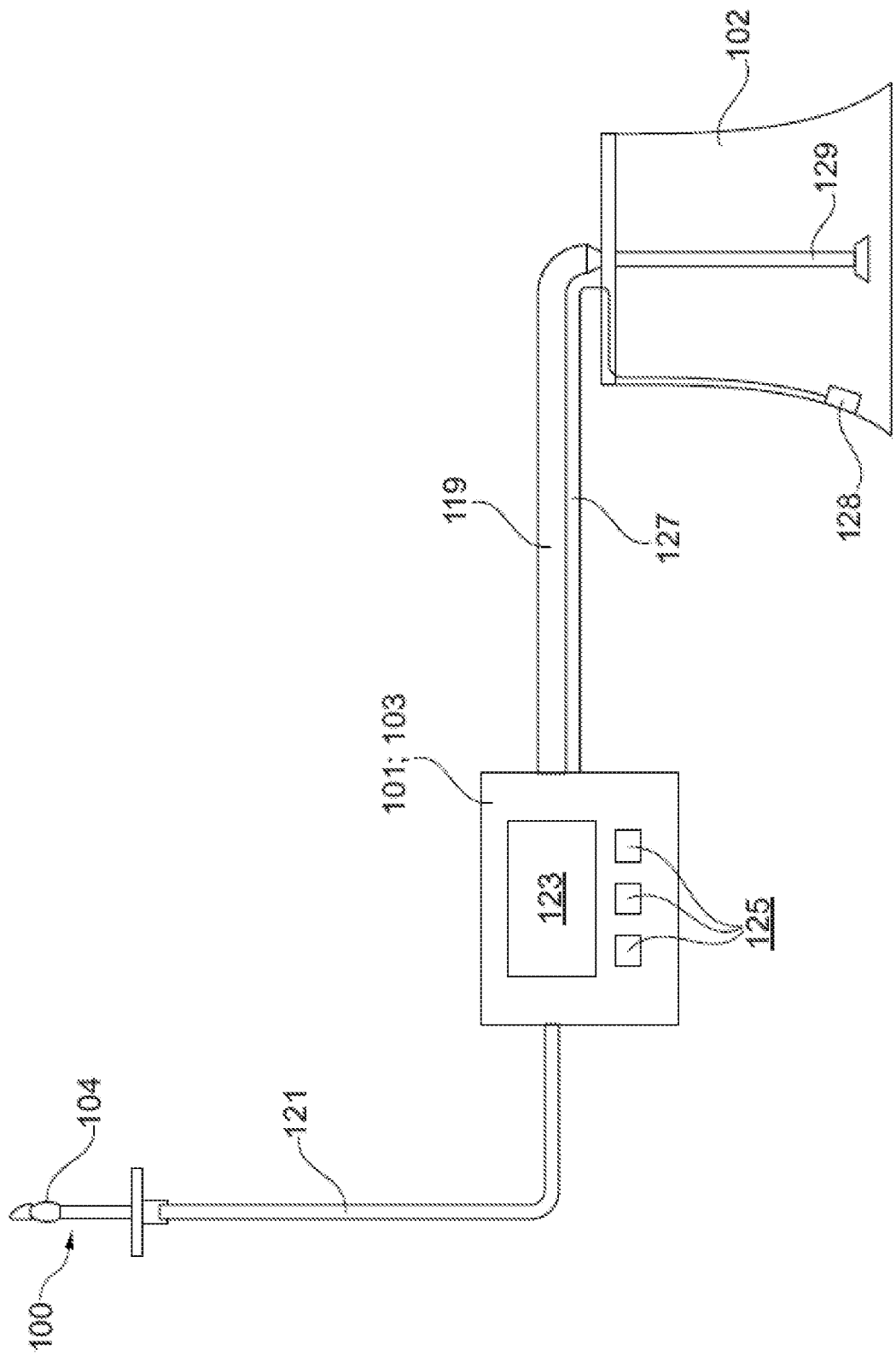
FIG. 1 shows an embodiment of a system for anal and/or stomal irrigation.

FIG. 1 shows an embodiment of a system for anal and/or stomal irrigation. The system comprises a catheter 100 sized and configured for insertion into the rectum or stoma of a user. A housing for a pump 101 is provided for transferring an irrigating liquid contained within a reservoir 102 to the catheter 100 and to an expandable retention element 104 in the form of a balloon configured to fixate the catheter within the user's rectum or stoma. A control system 103 for the pump and a valve system (not visible in FIG. 1) is further housed within the housing of the pump 101. Tube portion 119 connects the reservoir 102 to the pump 101, and tube portion 121 connects the pump within the housing of the pump 101 to the catheter 100 and expandable retention element 104. As discussed in further detail in relation to FIGS. 2-5 below, tube portion 121 includes separate conduits for connecting the pump to the catheter for expelling of irrigating liquid from the catheter tip and for expansion of the balloon 104, respectively. Tube portion 119 attaches to dip tube 129 for sucking irrigating liquid from the reservoir 102. The housing of the pump 101 is provided with a display 123 for communicating an operating state of the system and/or an asymptotic temperature value to the user, and user-operable control buttons 125 are provided as part of a user operable control interface for controlling operation of the valve system (not visible in FIG. 1) and/or pump 101. One of the user-operable control buttons 125 in FIG. 1 may be a dedicated emergency stop zone embodied as an emergency stop button for user-activated withdrawal of the irrigating liquid from the retention element 104 at any time. A thermo sensor 128 attaches to a wall of the reservoir 102, a wired connection 127 being provided for communicating a signal from the thermo sensor 128 to the control system 103 within housing of the pump 101.

Figure 2:
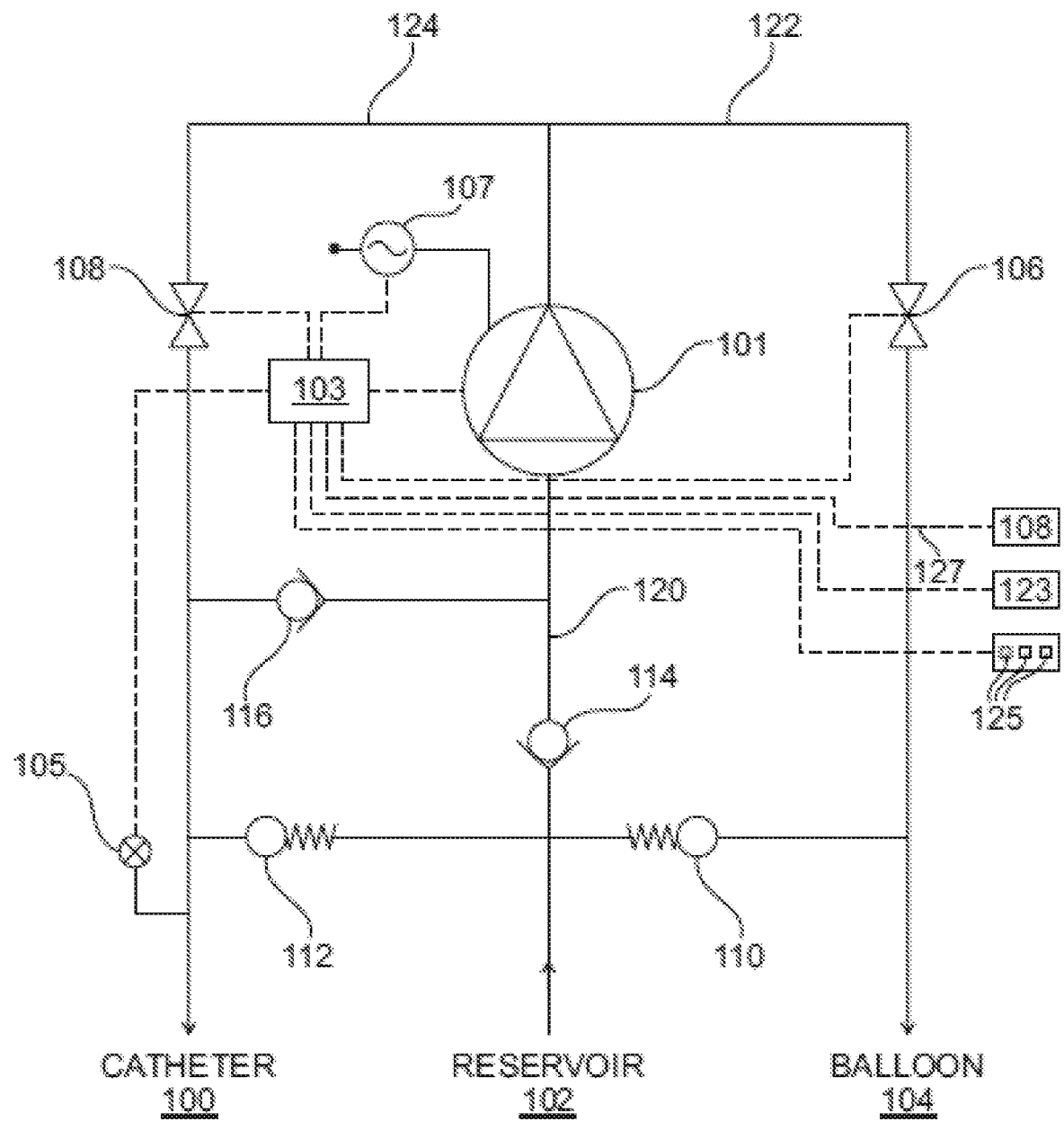
FIG. 2 shows an embodiment of a tubing and valve system of an embodiment of a system for anal and/or stomal.

FIG. 2 illustrates an embodiment of a tubing and valve system of the system of FIG. 1. As shown, pump 101 is connected to reservoir 102 via conduit 120 comprising a first check valve 114. The conduit 120 is provided within tube portion 119 (see FIG. 1). The first check valve 114 may be provided within tube portion 119, or within the housing of the pump 101, or within the dip tube 129. Downstream of the pump (when seen in flow direction from the reservoir towards the catheter 100 and the balloon 104), the tubing system has two branches, one of which includes conduit 122 connecting to the balloon 104 via a first actively controllable valve 106. The conduit 122 is provided within tube portion 121. The first actively operable valve 106 may be provided within the tube portion 121, or within the catheter 100, or within the housing of the pump 101. The other branch of the tubing system downstream of the pump includes conduit 124 connecting to the catheter 100 via a second actively controllable valve 108. The conduit 124 is provided within tube portion 121. The second actively operable valve 108 may be provided within the tube portion 121, or within the catheter 100, or within the housing of the pump 101. As shown by dashed lines in FIGS. 2-5, the actively controllable valves 106 and 108 are controllable by the control system 103.

A pressure sensor 105 is provided for measuring pressure at at least one first predetermined position in the tubing system 119, 120, 121, 122, 124 and/or the catheter 100 during operation of the pump 101. The pressure sensor 105 outputs a signal to the control system 103, which operates the pump and/or the actively controllable valves 106, 108 on the basis of said signal and other signals as described herein. The control system 103 includes a processor for determining or estimating a flow condition at the catheter tip on the basis of the measure of pressure provided by pressure sensor 105, and the control system is configured to control the pumping operation of the pump in response to said measure of pressure. More specifically, the control system continues pumping operation of the pump 101 for a limited period of time after determination, by the pressure sensor 105, of a pressure value which is at least equal to a pressure threshold value or a value derived therefrom. Thus, the amount of irrigating liquid expelled from the catheter tip may be accurately controlled. In the embodiment shown, the pressure sensor 105 is arranged in the tubing system 121, 124 in the vicinity of the catheter 100 or within the catheter 100 itself.

Control system 103 further receives input from user-operable control buttons 125, and thermo sensor 128, and control system 103 communicates data to display 123. The data communicated to display 123 may include a predicted future asymptotic value of the temperature of the irrigating liquid within the reservoir 102 as determined by thermo sensor 128. The data may be continuously updated as the control system 103 continuously updates the temperature prediction while irrigating liquid is being filled or re-filled into the reservoir.

First and second relief valves 110 and 112 are provided for allowing irrigating liquid to escape from the balloon 104 or from the catheter 100 in case the pressure therein exceeds the threshold pressure defined by the relief valves. The first relief valve 110 drains liquid from the balloon 104 to the reservoir 102 in the case of excessive pressure within the balloon 104, and the second relief valve drains liquid from the catheter 100 to the reservoir 102 in the case of excessive pressure within the user's rectum or stoma.

Further, first and second check valves 114 and 116 are provided for preventing undesired backflow of liquid in the tubing system. The first check valve 114 is provided within conduit 120 between the pump 101 and the reservoir 102 in order to prevent backflow of irrigating liquid from the pump 101, or any position downstream of the pump, to the reservoir 102. The second check valve 116 is provided in a side branch in the tubing system connecting conduit 124 to conduit 120. The first and second check valves 114 and 116 may be provided within tube portions 119 and 121 (see FIG. 1) or within the housing of the pump 101, or alternatively the first check valve 114 may be provided in dip tube 129. Second check valve 116 may be provided within the catheter 100.

Figure 3:
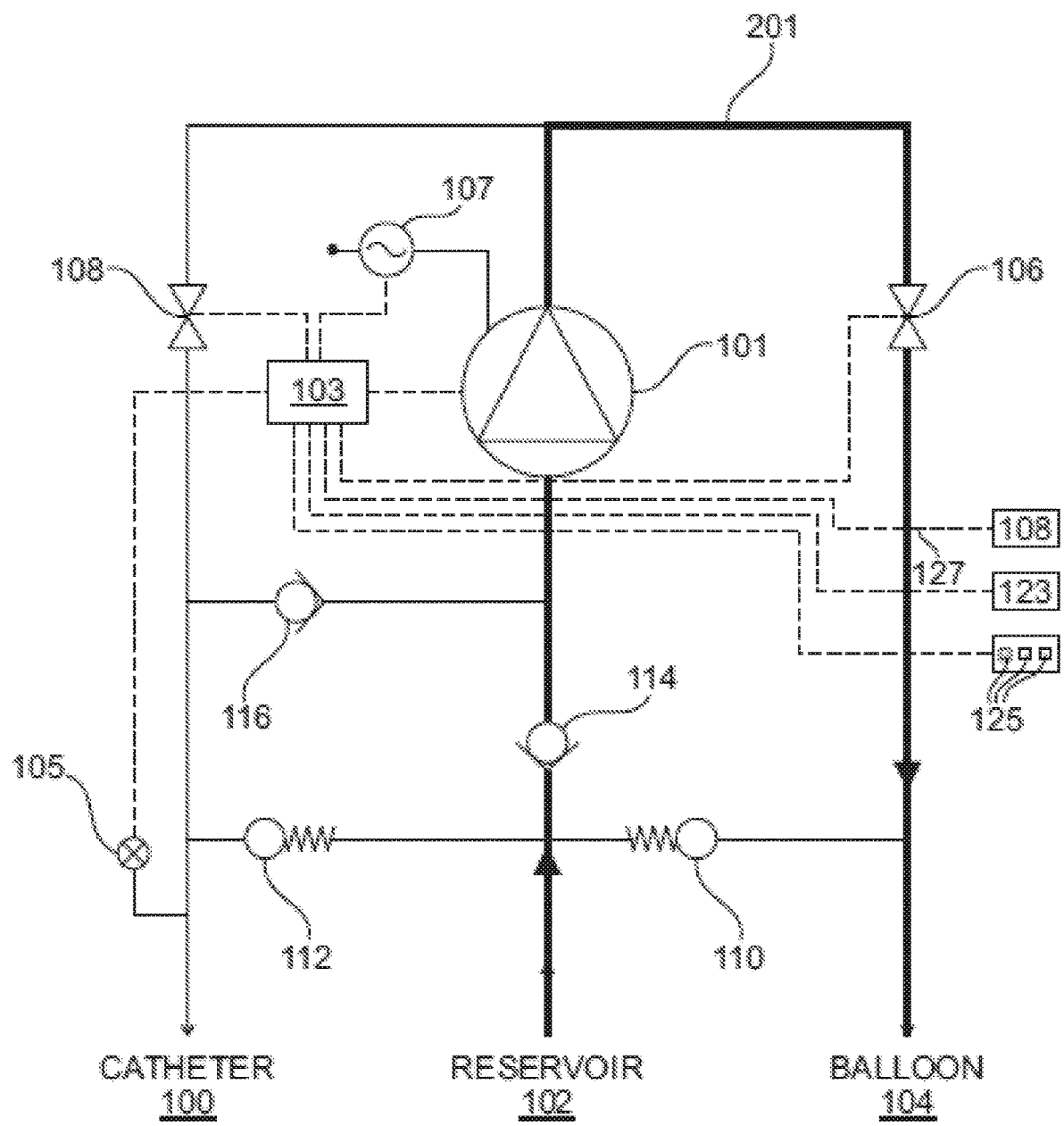
FIGS. 3-5 show respective embodiments of flow configurations in the tubing and valve system of FIG. 2.
Figure 4:
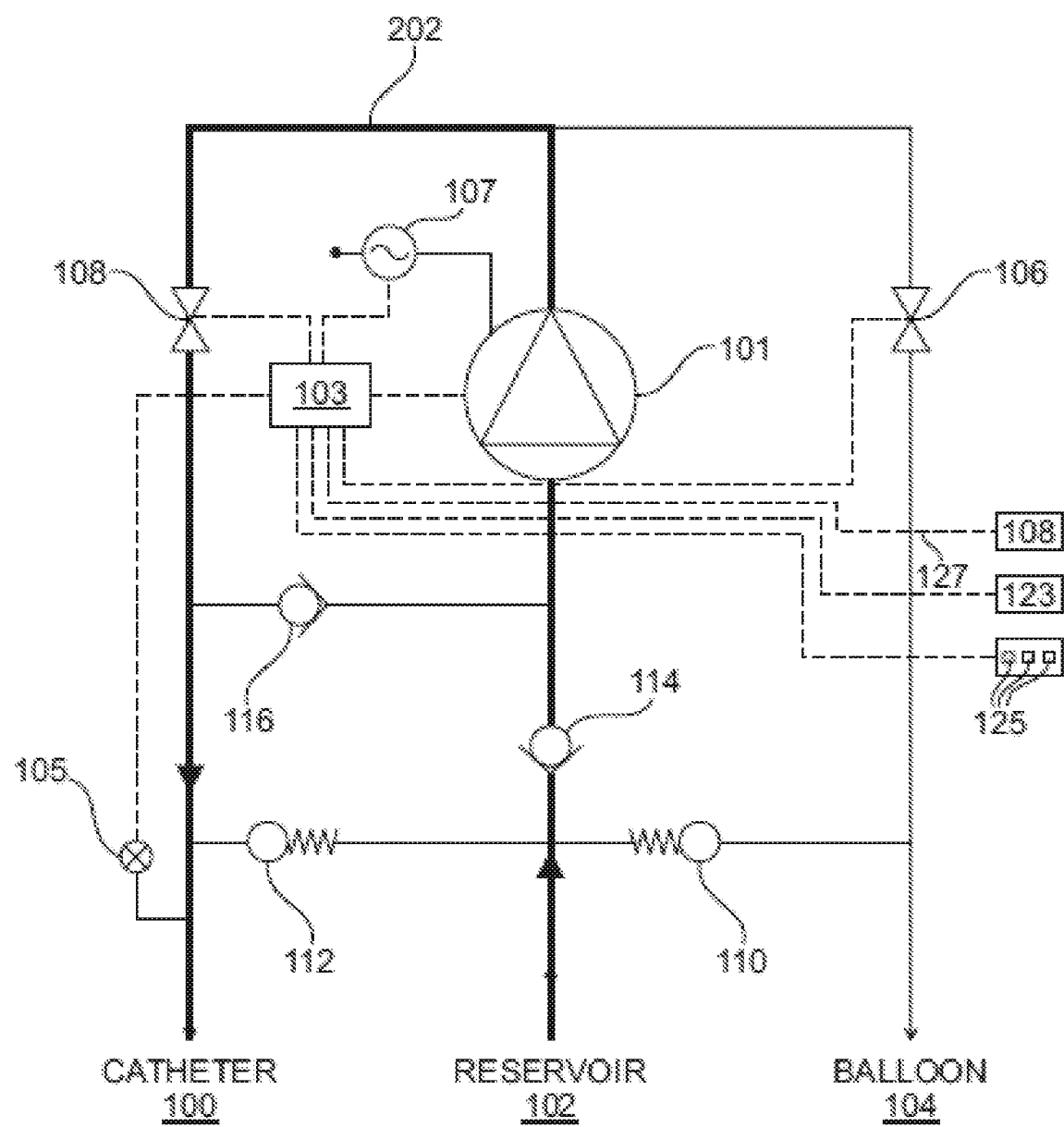
Figure 5:
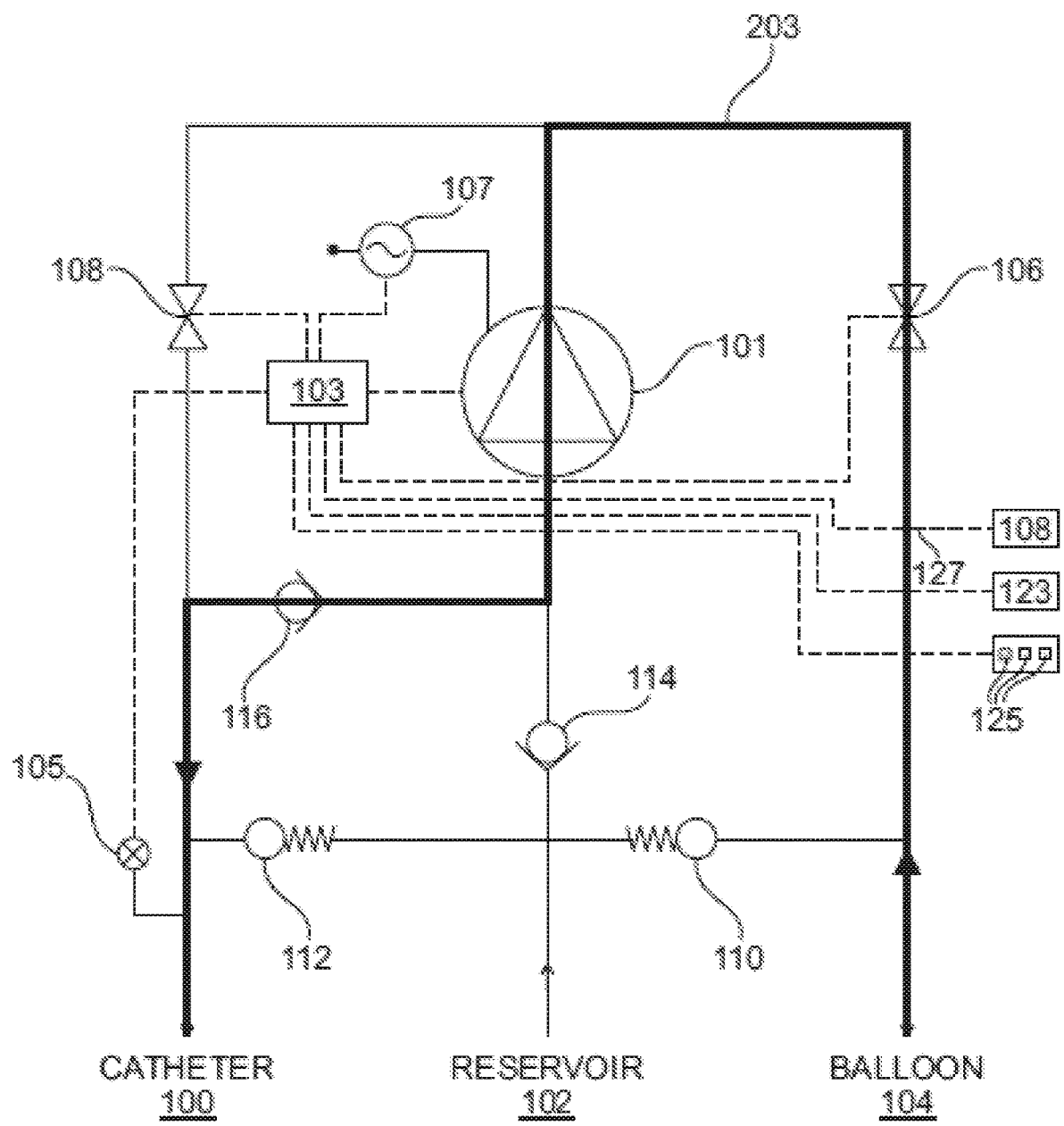

FIGS. 3-5 show respective embodiments of flow configurations in the tubing and valve system of FIG. 2. In the first flow configuration 201 shown in FIG. 3, the first actively controllable valve 106 is open, and the second actively controllable valve 108 is closed while the pump 101 operates. Accordingly, irrigating liquid is transferred from the reservoir 102 to the balloon 104 for expansion thereof. In the second flow configuration 202 shown in FIG. 4, the second actively controllable valve 108 is open, and the first actively controllable valve 106 is closed while the pump 101 operates. Irrigating liquid is thus transferred from the reservoir 102 to the catheter 100, at the tip of which the liquid is expelled into the user's rectum or stoma so as to irrigate the user's bowel. In the third flow configuration 203 shown in FIG. 5, operation of the pump 101 is reversed, and the first actively controllable valve 106 is open, while the second actively controllable valve 108 is closed. The balloon 104 is hence purged, and the irrigating liquid withdrawn therefrom flows from the balloon 104 to the catheter 100, at the tip of which it is expelled.

Figure 5A:
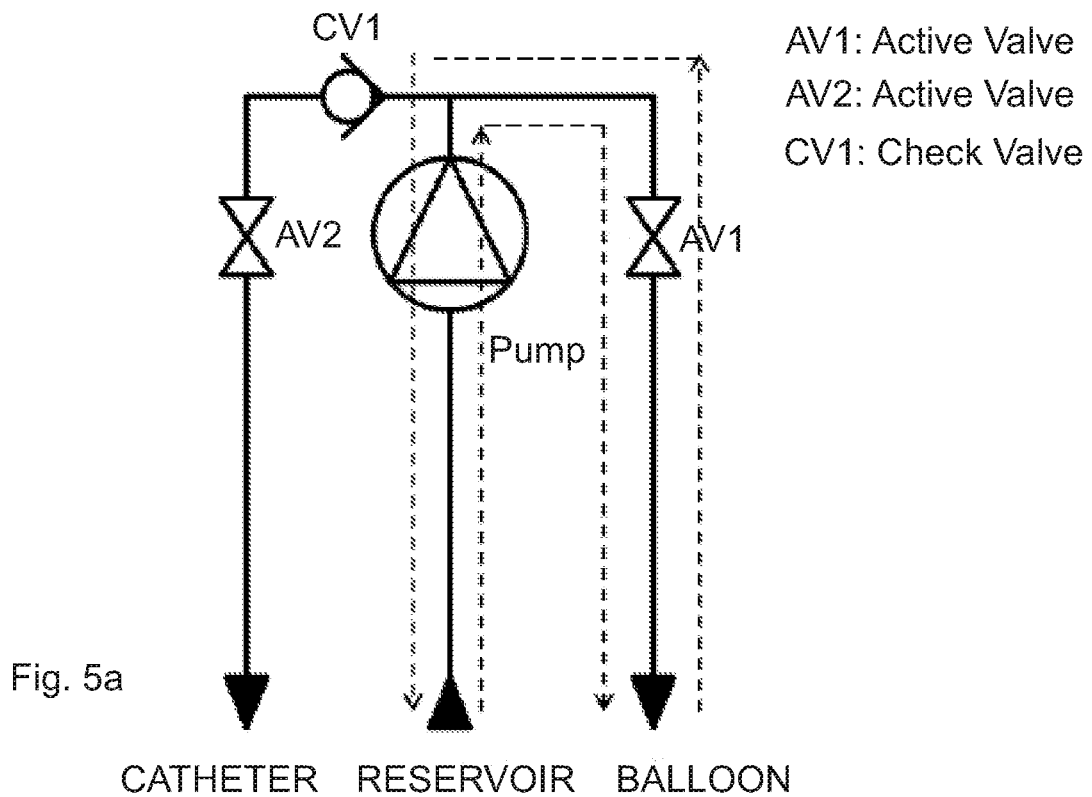
FIGS. 5a and 5b show embodiments of flow configurations in an alternative embodiment.
Figure 5B:
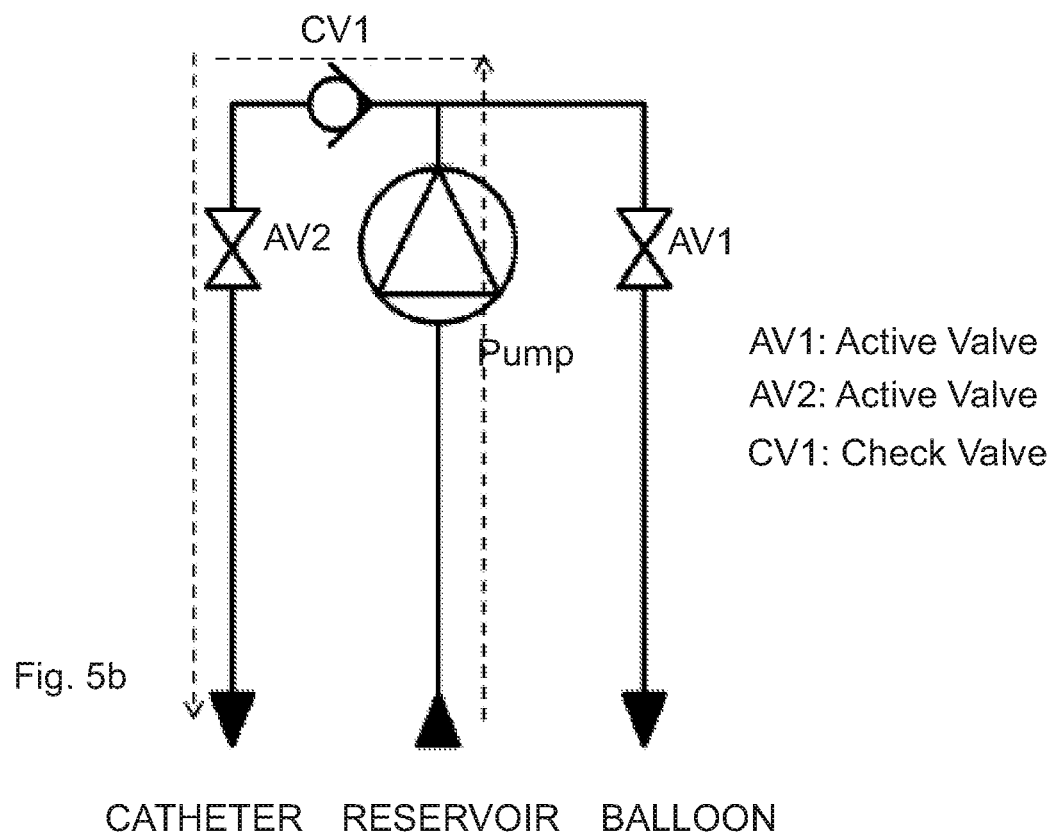

In the alternative embodiment of FIGS. 5a and 5b, in which the balloon 104 may be emptied into the reservoir 102 by forced action of the pump 101. The dashed lines in FIGS. 5a and 5b indicate respective flow configurations for expanding the balloon and purging thereof into the reservoir. FIG. 5b indicates a flow configuration for expelling of the irrigating liquid through the catheter. In the flow configurations of FIG. 5a, a first actively controlled valve AV1 is open, and a second actively controlled valve AV2 is closed. For expansion of the balloon, the pump 101 operates in a first operating direction, whereas for purging, i.e. collapsing of the balloon, the pump 101 operates in a second operating direction opposite to the first operating direction. In the flow configuration of FIG. 5b, the first actively controlled valve AV1 is closed, and the second actively controlled valve AV2 is open. Check-valve CV1 prevents backflow of the irrigating liquid from the catheter tubing conduit towards the reservoir.

Figure 6:
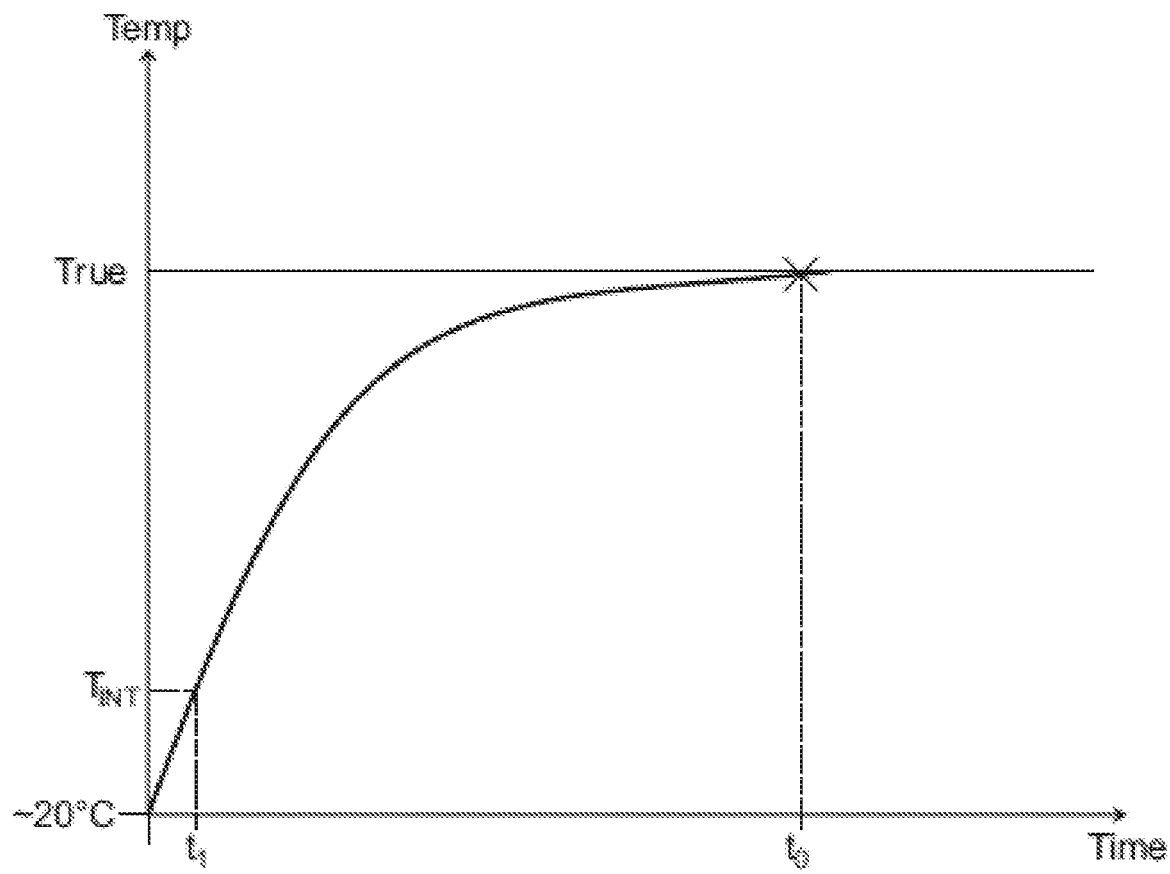
FIGS. 6 and 7 illustrates exemplary curves of temperature of an irrigating liquid in a reservoir during filling or refilling of irrigating liquid into the reservoir.
Figure 7:
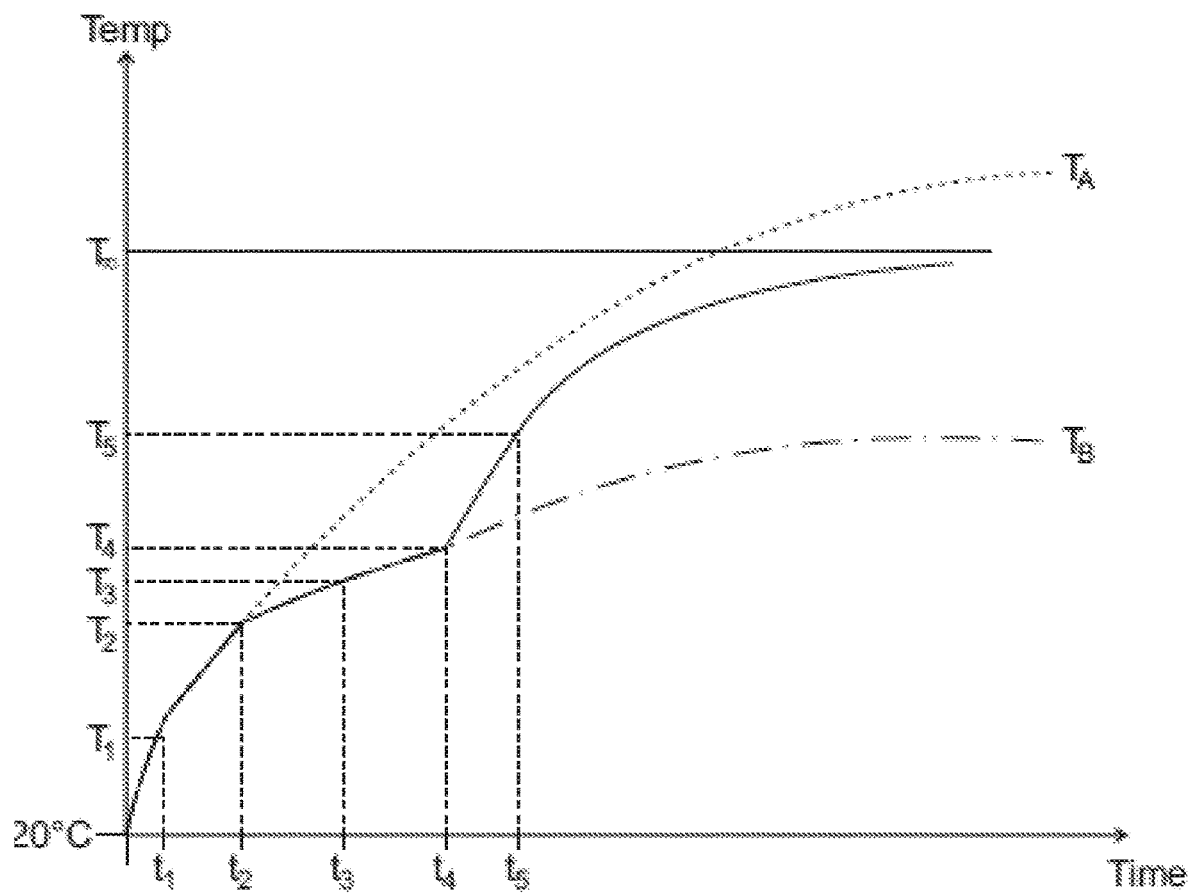

FIGS. 6 and 7 illustrates exemplary curves of temperature of the irrigating liquid in the reservoir 102 during filling or refilling of irrigating liquid into the reservoir. In the chart of FIG. 6, the initial temperature of the irrigating liquid within the reservoir 102 as determined by thermo sensor 128 is approximately 20° C. As the user's bowel should be irrigated with liquid at a temperature not exceeding approximately 40° C., preferably at a temperature of 20-40° C., most preferably at a temperature of 36-38° C., the user starts pouring liquid, such as tap water, at an elevated temperature into the reservoir.

Next, an initial change of the temperature within the reservoir is determined by the thermo sensor 128 upon commencement of filling or refilling of the irrigating liquid into the reservoir 120. In FIG. 6, the initial temperature change is represented by elevated temperature TINT at time L. On the basis of the initial temperature change, a future asymptotic value of the temperature, denoted "True" in FIG. 6, within the reservoir is predicted on the basis of at least the initial change.

As shown in FIG. 7, a current temperature or a current rate of change of the temperature within the reservoir is continuously determined by means of thermo sensor 128 and control system 103, while the irrigating liquid is filled or refilled into the reservoir, and the prediction of the future asymptotic value of the temperature within the reservoir is continuously updated on the basis of at least said current temperature and/or rate of change of the temperature. More specifically, at the start of the filling or refiling procedure, an initial temperature change $T_1$ is determined at a first point in time, $t_1$. The first initial temperature change as represented by $T_1$ is used for a first prediction, $T_A$, of a future asymptotic temperature value of the irrigating liquid within the reservoir 102 once filled. At a second point in time, $t_2$, when the temperature as determined by the thermo sensor 128 has reached level $T_2$, the temperature of the liquid supplied to the reservoir changes, for example as the user changes the ratio of hot to cold water in the tap. At a third point in time $t_3$, a third temperature value $T_3$ is obtained, and second prediction $T_B$ is made. Subsequently, at a fourth point in time, $t_4$, a fourth temperature level $T_4$ is reached, and the temperature of the liquid filled into the reservoir 102 changes abruptly for a second time. The change of the supplied liquid is reflected by temperature $T_5$ at time $t_5$, on the basis of which a third asymptotic temperature prediction $T_\infty$ is made.

During the above procedure, the predicted temperature values $T_A$, $T_B$ and $T_\infty$ are shown to the user via display 123 (see FIGS. 1-5) as they are determined by the control system 103.

Figure 8:
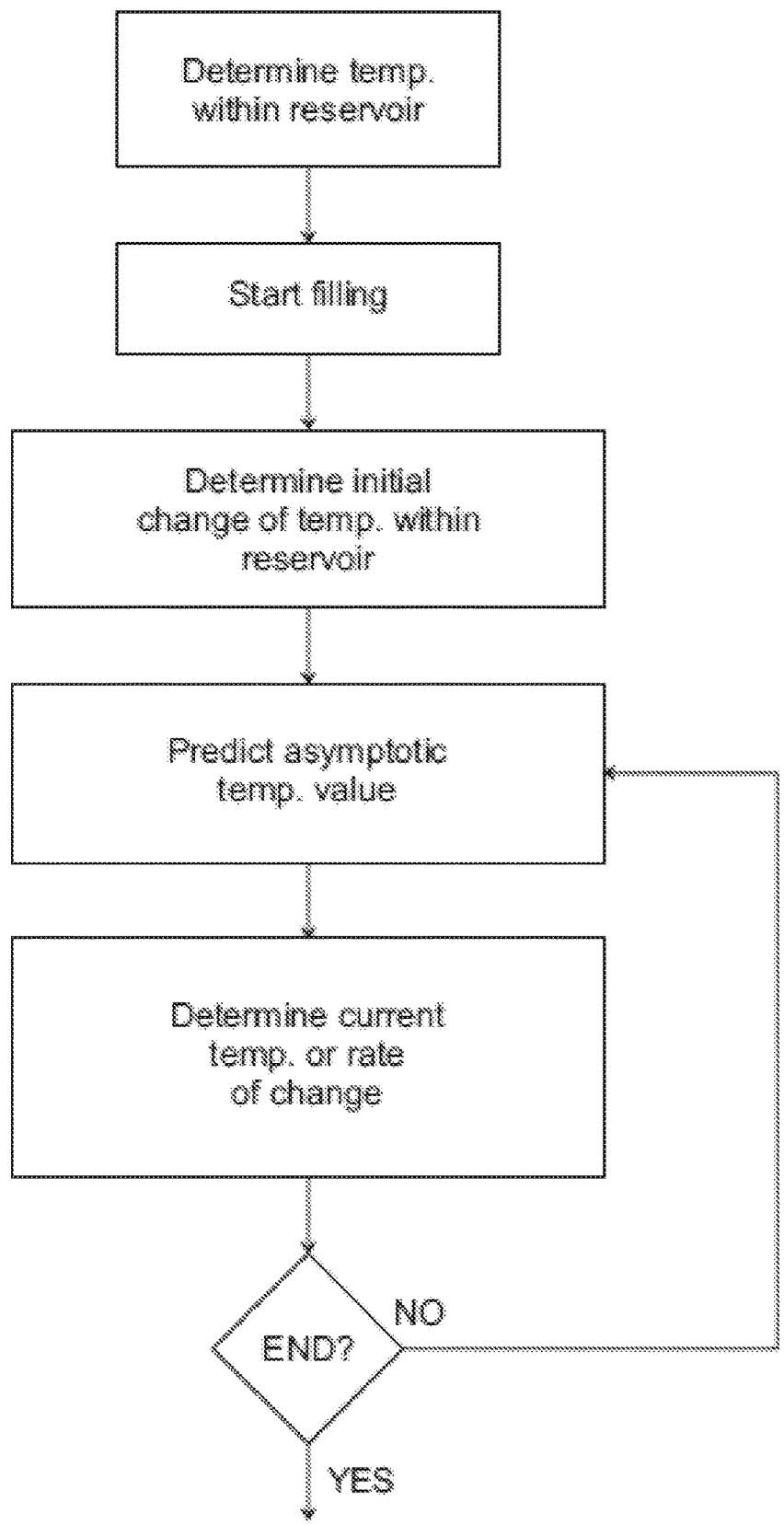
FIG. 8 illustrates a method for predicting a temperature of an irrigating liquid in a reservoir of a system for anal irrigation.

The above procedure of continuously determining and updating the asymptotic temperature prediction is generally depicted in FIG. 8.

FIGS. 9a-15b illustrates display configurations of a graphical user interface of a user-operable control interface. It should be understood that a dedicated emergency stop zone (not shown in FIGS. 9a-15b) may be provided in relation to all of the graphical user displays shown in FIGS. 9a-15b. The dedicated emergency stop zone may e.g. be provided in the form of a mechanically activated button or switch 125 (see FIG. 1), or a dedicated area of a touchscreen. The display configurations of FIGS. 9a-15b are shown in the display 123 of the system (see FIG. 1).

FIGS. 9a-9c are initial screen displays presented to the user upon initialization and setup of the system. The user is allowed to choose the size of the retention element, i.e. balloon (FIG. 9a), confirm settings (FIG. 9b), and set various system settings, including language, units, etc. (FIG. 9c).

FIGS. 10a-10c are screen displays presented to the user during start-up of the system, including a general start-up indication (FIG. 10a), battery status (FIG. 10b), and an instruction to the user to commence filling the irrigating liquid, such as tap water into the reservoir, i.e. container (FIG. 10c).

FIGS. 11a-11d illustrate display configurations related to temperature indications of the irrigating liquid in the reservoir, including information advising that temperature measurement is ongoing (FIG. 11a), inadequate temperature, i.e. too hot or too low (FIGS. 11b and 11c, respectively), and adequate temperature (FIG. 11d).

FIGS. 12a and 12b illustrate instructions in the graphical user interface for the user to connect the catheter to the tubing system (FIG. 12a), and to start the pump for the irrigating liquid (FIG. 12b).

Figure 13:

FIG. 13 illustrates a low-battery status indication in the display of the graphical user interface.

Figure 14A:
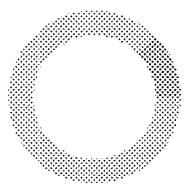
Figure 14B:
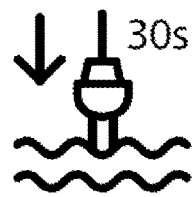
Figure 14C:
Figure 14D:
Figure 14E:
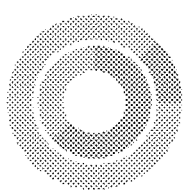
Figure 14F:
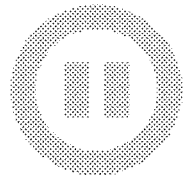
Figure 14G:
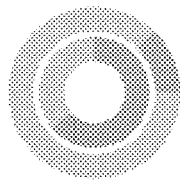
Figure 14H:
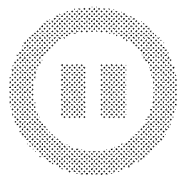
Figure 14I:
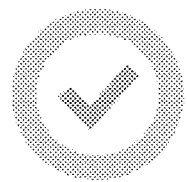
Figure 14J:
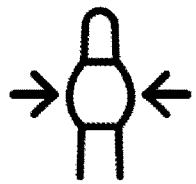
Figure 14K:
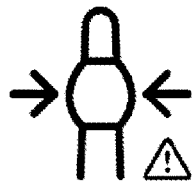

FIGS. 14a-14r are illustrations of display occurring during an irrigating cycle, including an indication that the tubes of the tubing system are being filled (FIG. 14a), instructions to the user to lubricate the catheter (FIG. 14b), and instructions to insert the catheter in the stoma or rectum (FIG. 14c). The user is further allowed to set the amount of irrigating liquid to be infused during irrigation (FIG. 14d). An indication may be provided in the graphical user interface of the process of inflation of the retention element, i.e. the balloon (FIG. 14e). A filling pause may be indicated (FIG. 14f), irrigating liquid infusion, infusion pausing and infusion completion may be indicated (FIGS. 14g, 14h, and 14i, respectively). Upon completion of infusion, instructions are provided to withdraw the irrigating liquid from the retention element, i.e. to empty the balloon (FIG. 14j). Retention element emptying status may be provided in the display of the graphical user interface (FIGS. 14k-14m), and upon completion of withdrawal of the irrigating liquid from the retention element, instructions may be provided for removal of the catheter from the stoma or rectum (FIG. 14n). Clean up instructions may be provided (FIG. 14o), and tube drainage status may be displayed (FIG. 14p). An end of session may further be displayed (FIG. 14r).

FIGS. 15a and 15b are general system notifications and alerts of a due system replacement (FIG. 15a) and system failure (FIG. 15b).

The invention claimed is:

1. A system for anal and stomal irrigation, the system comprising:
    a reservoir adapted to contain an irrigating liquid;
    a catheter comprising an expandable retention element configured to retain the catheter in one of the rectum and the stoma;
    a tubing system including a first conduit for transport of the irrigating liquid between the reservoir and the catheter and a second conduit for transport of the irrigating liquid between the reservoir and the expandable retention element;
    a valve system in the second conduit for controlling the transport of the irrigating liquid between the reservoir and the expandable retention element;
    a pump operable to pump the irrigating liquid from the reservoir to the catheter tip, with the pump and the valve system configured to selectively:
    pump the irrigating liquid into the expandable retention element;
    pump the irrigating liquid out of the catheter for irrigation of one of the rectum and the stoma; and
    withdraw the irrigating liquid from the expandable retention element and return the irrigating liquid withdrawn from the expandable retention element to the reservoir; and
    a control interface for operation of the system;
    wherein the pump is a reversible electrical pump that is operable in a first direction to pump the irrigating liquid into the expandable retention element and in a second reverse direction to withdraw the irrigating liquid from the expandable retention element and return the irrigating liquid withdrawn from the expandable retention element to the reservoir.

2. The system of claim 1, wherein the control interface for operation of the system comprises a dedicated emergency stop zone and wherein in response to input from a user, the dedicated emergency stop zone operates the pump and the valve system to withdraw the irrigating liquid from the expandable retention element.

3. The system as in claim 2, wherein the control interface is configured to recognize a single input from the user for activation of the dedicated emergency stop zone.

4. The system as in claim 2, wherein the dedicated emergency stop zone is a push button.

5. The system as in claim 2, wherein the dedicated emergency stop zone is a mechanical button.

6. The system as in claim 1, wherein the control interface comprises a graphical user interface.

7. The system as in claim 6, wherein the graphical user-interface is configured to notify the user if a temperature of the irrigating fluid is outside a predetermined temperature interval.

8. The system as in claim 6, wherein the control interface comprises user operation instructions and the graphical user-interface is configured to display the user operation instructions.

9. The system as in claim 6, wherein the graphical user-interface is configured to display a system operational state status.

10. The system as in claim 6, wherein the graphical user-interface is configured to notify the user that a cleaning sequence is scheduled.

11. The system as in claim 6, wherein the graphical user-interface is configured to notify the user that the system is scheduled to be replaced after a predetermined number of operational cycles.

* * * * *

UNITED STATES PATENT AND TRADEMARK OFFICE
CERTIFICATE OF CORRECTION

PATENT NO. : 11,083,834 B2
APPLICATION NO. : 16/062111
DATED : August 10, 2021
INVENTOR(S) : Falleboe et al.

It is certified that error appears in the above-identified patent and that said Letters Patent is hereby corrected as shown below:

On the Title Page

In item [57], in Column 2, Line 11, delete "retention element (100)" and insert -- retention element (104) --, therefor.

In the Drawings

Fig. 10c, Sheet 10 of 15, delete "Preperation" and insert -- Preparation --, therefor.

Fig. 10c, Sheet 10 of 15, delete "wih" and insert -- with --, therefor.

Fig. 12a, Sheet 11 of 15, delete "Preperation" and insert -- Preparation --, therefor.

Fig. 12b, Sheet 11 of 15, delete "Preperation" and insert -- Preparation --, therefor.

In the Specification

Column 3, Line 2, delete "be" and insert -- by --, therefor.

Column 4, Line 2, delete "be" and insert -- by --, therefor.

Column 6, Line 3, delete "number" and insert -- number of --, therefor.

Column 6, Line 11, delete "the irrigating" and insert -- of the irrigating --, therefor.

Column 8, Line 24, delete "illustrates" and insert -- illustrate --, therefor.

Column 8, Line 30, delete "illustrates" and insert -- illustrate --, therefor.

Column 10, Line 51, delete "illustrates" and insert -- illustrate --, therefor.

Signed and Sealed this
Thirtieth Day of November, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 11,083,834 B2

Column 10, Line 65, delete "reservoir 120." and insert -- reservoir 102. --, therefor.

Column 10, Line 66, delete "TINT" and insert -- $T_{INT}$ --, therefor.

Column 10, Line 67, delete "L." and insert -- $t_1$. --, therefor.

Column 11, Line 39, delete "illustrates" and insert -- illustrate --, therefor.

In the Claims

Column 12, Line 50, in Claim 1, delete "catheter tip," and insert -- catheter, --, therefor.